(12) United States Patent
Jacobs et al.

(10) Patent No.: US 6,372,455 B1
(45) Date of Patent: Apr. 16, 2002

(54) RECOMBINANT VACCINIA VIRAL VECTORS

(75) Inventors: Bertram Jacobs, Tempe; Jeffrey Langland, Mesa; Sangeetha Vijaysri, Tempe, all of AZ (US)

(73) Assignee: Arizona Board of Regents, Tempe, AZ (US)

( * ) Notice: Subject to any disclaimer, the term of this patent is extended or adjusted under 35 U.S.C. 154(b) by 0 days.

(21) Appl. No.: 09/837,997

(22) Filed: Apr. 19, 2001

(51) Int. Cl.[7] ............................ C12P 21/06; C12Q 1/70; C12N 15/00; C07H 21/04
(52) U.S. Cl. ...................... 435/69.1; 435/5; 435/320.1; 536/23.72
(58) Field of Search ....................... 435/5, 320.1, 69.1; 536/23.72

(56) References Cited

U.S. PATENT DOCUMENTS 6,004,777 A  12/1999  Tartaglia et al. ............ 435/69.1

FOREIGN PATENT DOCUMENTS

WO        0073487       12/2000

OTHER PUBLICATIONS

U.S. Patent Application No. 09/887,295 to Jacobs et al., filed Jun. 22, 2001.
Beattie et al., "Reversal of the Interferon–Sensitive Phenotype of a Vaccinia Virus Lacking E3L by Expression of the Reovirus S4 Gene", Journal of Virology, vol. 69, No. 1, Jan. 1995, pp. 499–505.

Shors et al., "Complementation of Vaccinia Virus Deleted of the E3L Gene by Mutants of E3L", Virology 239:269–276, 1997.

Chang et al., "Identification of a Conserved Motif That is Necessary for Binding of the Vaccinia Virus E3L Gene Products to Double–Stranded RNA", Virology 194:573–547.

Brandt et al., "Both Carboxy–and Amino–Terminal Domains of the Vaccinia Virus Interferon Resistance Gene, E3L, Are Required for Pathogenesis in a Mouse Model", J. Virology 75:850–856, 2001.

McInnes et al., "Orf Virus Encodes a Homolog of the Vaccinia Virus Interferon–Resistance Gene E3L", Virus Genes 17:2, pp107–115. 1998.

Kibler et al., "Double–Stranded RNA Is a Trigger for Apoptosis in Vaccinia Virus–Infected Cells", J. Virology 71:1992–2003, 1997.

U.S. patent application, serial No. 09/837,998.

Primary Examiner—Hankyel T. Park
(74) Attorney, Agent, or Firm—Baker Botts L.L.P.

(57) ABSTRACT

The present invention provides recombinant vaccinia virus in which the E3L gene is replaced by a gene encoding an E3L homolog from the orf virus. Compositions comprising the recombinant vaccinia virus and methods of use thereof are also provided.

7 Claims, 4 Drawing Sheets

FIG. 4

RECOMBINANT VACCINIA VIRAL VECTORS

BACKGROUND OF THE INVENTION

Vaccinia virus is a member of the poxvirus family of DNA viruses. Poxviruses including vaccinia virus are extensively used as expression vectors since the recombinant viruses are relatively easy to isolate, have a wide host range, and can accommodate large amounts of DNA.

The vaccinia virus genome contains nonessential regions into which exogenous DNA can be incorporated. Exogenous DNA can be inserted into the vaccinia virus genome by well-known methods of homologous recombination. The resulting recombinant vaccinia viruses are useful as vaccines and anticancer agents.

The use of vaccinia virus recombinants as expression vectors and particularly as vaccines and anticancer agents raises safety considerations associated with introducing live recombinant viruses into the environment. Virulence of vaccinia virus recombinants in a variety of host systems has been attenuated by the deletion or inactivation of certain vaccinia virus genes that are nonessential for virus growth. However, there remains a need in the art for the development of vectors that have reduced pathogenicity while maintaining desirable properties of wild-type virus, such as host range, and active protein synthesis of a desired gene product.

SUMMARY OF THE INVENTION

The present invention provides a recombinant vaccinia virus in which the vaccinia virus E3L gene is replaced by a gene encoding an E3L homolog from the orf virus. The invention further provides an expression vector comprising the recombinant vaccinia virus and exogenous DNA, and methods of use of the recombinant vaccinia virus.

BRIEF DESCRIPTION OF THE DRAWING

FIG. 4 is a graph depicting weight change in vaccinated and unvaccinated mice after challenge with wild-type virus.

DETAILED DESCRIPTION OF THE INVENTION

Figure 1:
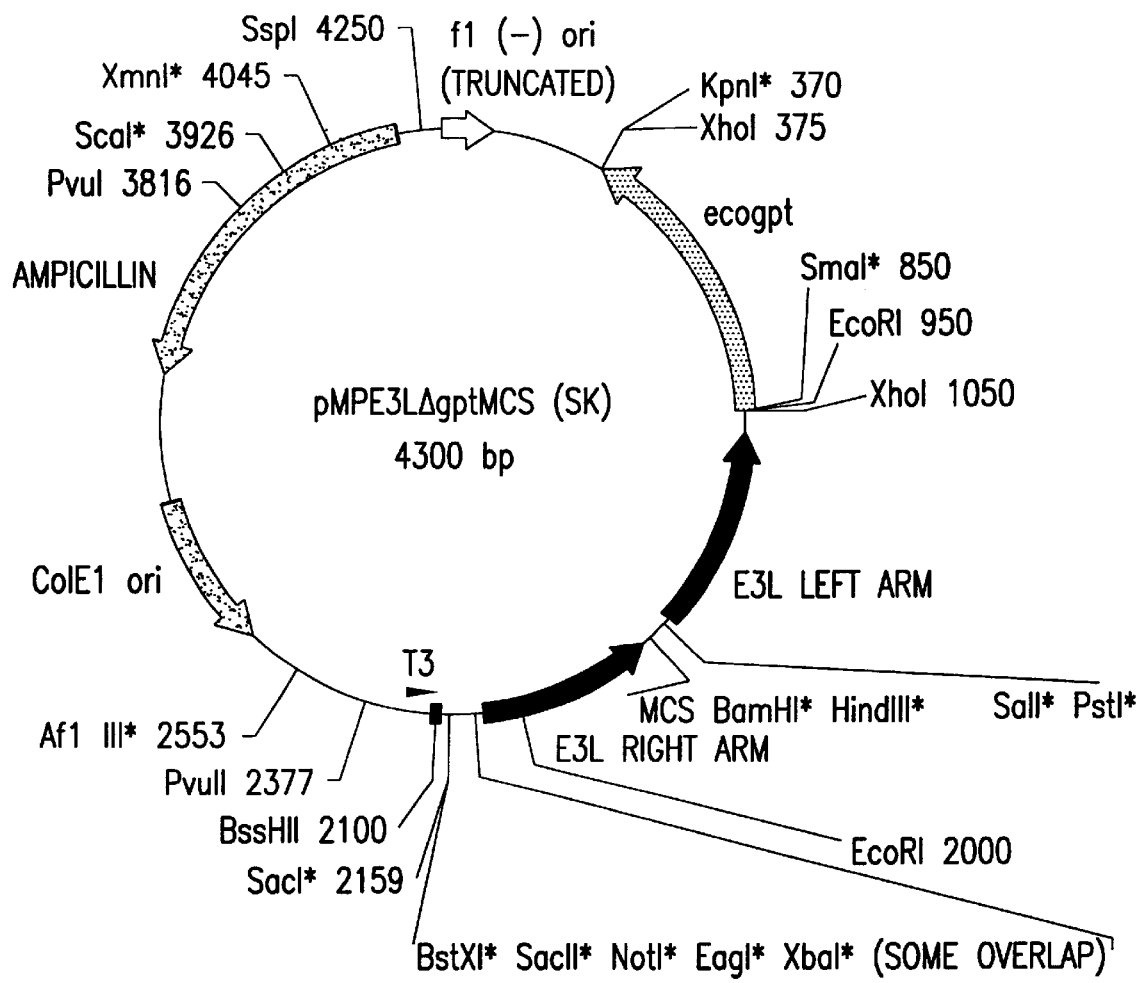
FIG. 1 depicts plasmid pMPEΔGPT. Restriction sites are estimated but are in the correct relative positions

The E3L gene product of the vaccinia virus is a 190 amino acid polypeptide. The E3L gene codes for several functions including a dsRNA-binding protein, a Z-DNA-binding protein, and dimerization. Amino acids 118–190 have been implicated in dsRNA binding, as disclosed by Kibler et al. (1997) *J. Virol.* 71: 1992, incorporated herein by reference. Amino acid numbering as used herein is adopted from Goebel et al. (1990) *Virology* 179: 247–66, 577–63, the disclosure of which is incorporated herein by reference.

It has been discovered in accordance with the present invention that recombinant vaccinia viruses in which the E3L gene is replaced by a gene encoding an E3L homolog from the orf virus are immunogenic but have decreased pathogenicity in mice relative to wild-type vaccinia virus. When administered intranasally, the recombinant viruses of the present invention replicate to high titers in nasal tissues, but do not spread to the lung or brain and have reduced neurovirolence.

The orf virus is a poxvirus of the genus parapoxvirus that infects sheep, goats and humans. Disease in humans is rare and usually mild and self-limiting. The orf virus contains a gene exhibiting sequence similarity to the vaccinia virus E3L gene. The gene is located 20 kilobases from the left terminus of the orf virus genome, and encodes a product having a predicted amino acid sequence exhibiting 31% identity and 57% similarity with the vaccinia virus E3L gene. The orf virus E3L homolog is known in the art and disclosed for example by McInnes et al. (1998) Virus Genes 17: 107–115, the disclosure of which is incorporated herein by reference.

The present invention firther provides recombinant vaccinia viral vectors comprising the recombinant vaccinia virus described above and further containing additional exogenous, i.e., nonvaccinia virus, DNA. Exogenous DNA may encode any desired product, including for example, an antigen, an anticancer agent, or a marker or reporter gene product. The recombinant vaccinia virus may further have deletions or inactivations of nonessential virus-encoded gene functions. Nonessential gene functions are those which are not required for viral replication in a host cell. The exogenous DNA is preferably operably linled to regulatory elements that control expression thereof. The regulatory elements are preferably derived from vaccinia virus.

The recombinant vaccinia virus of the present invention may be constructed by methods known in the art, for example by homologous recombination. Standard homologous recombination techniques utilize transfection with DNA fragments or plasmids containing sequences homologous to viral DNA, and infection with wild-type or recombinant vaccinia virus, to achieve recombination in infected cells. Conventional marker rescue techniques may be used to identify recombinant vaccinia virus. Representative methods for production of recombinant vaccinia virus by homologous recombination are disclosed by Piccini et al. (1987) *Methods in Enzymology* 153:545, the disclosure of which is incorporated herein by reference.

For example, the recombinant vaccinia virus of a preferred embodiment of the present invention may be constructed by infecting host cells with vaccinia virus from which the E3L gene has been deleted, and transfecting the host cells with a plasmid containing a nucleic acid encoding the orf virus E3L homolog flanked by sequences homologous to the left and right arms that flank the vaccinia virus E3L gene. The vaccinia virus used for preparing the recombinant vaccinia virus of the invention may be a naturally occurring or engineered strain. Strains useful as human and veterinary vaccines are particularly preferred and are well-known and commercially available. Such strains include Wyeth, Lister, W R, and engineered deletion mutants of Copenhagen such as those disclosed in U.S. Pat. No. 5,762,938, which is incorporated herein by reference. Recombination plasmids may be made by standard methods known in the art. The nucleic acid sequences of the vaccinia virus E3L gene and the left and right flanking arms are well-known in the art, and may be found for example, in Earl et al. (1993) in *Genetic Maps: locus maps of complex genomes*, O'Brien, ed., Cold Spring Harbor Laboratory Press, 1.157 the disclosure of which is incorporated by reference, and Goebel et al. (1990), supra. The amino acid numbering used herein is adopted from Goebel et al. (1990), supra. The vaccinia virus used for recombination may contain other deletions, inactivations, or exogenous DNA as described hereinabove. The nucleic acid sequence encoding the orf virus E3L homolog is disclosed by McInnes et al., supra.

Following infection and transfection, recombinants can be identified by selection for the presence or absence of markers on the vaccinia virus and plasmid. Recombinant vaccinia virus may be extracted from the host cells by standard methods, for example by rounds of freezing and thawing.

The resulting recombinant vaccinia virus may be further modified by homologous recombination to provide other deletions, inactivations, or to insert exogenous DNA.

It has been discovered in accordance with the present invention that a recombinant vaccinia virus in which the E3L gene is replaced by a gene encoding an E3L homolog from the orf virus maintains viral replication, protein synthesis, interferon-resistance and cell tropism that is indistinguishable from wild-type virus, but has remarkably reduced pathogenicity in mice relative to wild-type vaccinia virus of the same strain.

The present invention further provides a composition comprising the recombinant vaccinia viral vector of the invention and a carrier. The term carrier as used herein includes any and all solvents, diluents, dispersion media, antibacterial and antifungal agents, microcapsules, liposomes, cationic lipid carriers, isotonic and absorption delaying agents, and the like.

The recombinant vaccinia viruses and compositions of the present invention may be used as expression vectors in vitro for the production of recombinant gene products, or as delivery systems for gene products, as human or veterinary vaccines, or anticancer agents. Such utilities for recombinant vaccinia viruses are known in the art, and disclosed for example by Moss (1996) "Poxviridae: The Viruses and Their Replication" in *Virology,* Fields et al., eds., Lippincott-Raven, Philadelphia, pp. 2637–2671, incorporated herein by reference.

The present invention further provides a method of making a recombinant gene product comprising subjecting a recombinant vaccinia viral vector comprising a vaccinia virus in which the E3L gene is replaced by a gene encoding an E3L homolog from the orf virus and further comprising exogenous DNA that encodes the recombinant gene product operably linked to the control of regulatory elements that control expression thereof, to conditions whereby said recombinant gene product is expressed, and optionally recovering the recombinant gene product. In a preferred embodiment, the recombinant gene product is an antigen that induces an antigenic and/or immunogenic response when the gene product or a vector that expresses it is administered to a mammal.

All references cited herein are incorporated in their entirety.

The following nonlimiting examples serve to further illustrate the invention.

EXAMPLE 1

Construction of Recombinant Vaccinia Virus

The plasmid pMPE3ΔGPTMCS (described by Kibler et al. (1997) *J. Virol.* 71: 1992, incorporated herein by reference) was used for recombining an orf virus E3L gene into the E3L locus of the WR strain of vaccinia virus. The recombination plasmid pMPE3ΔGPT (provided by Virogenetics) is a derivative of pBSIISK (Stratagene, La Jolla, Calif.) that has had the β-galactosidase sequences deleted, and that contains sequences homologous to the left and right arms flanking the vaccinia virus E3L gene, but that lacks the E3L gene itself. The recombination plasmid contains the *E. coli* gpt gene outside the E3L flanking arms and thus allows for selection of transfected cells by treatment with mycophenolic acid (MPA). The plasmid pMPE3ΔGPT was altered by the addition of a multiple cloning site to create pMPE3ΔGPTMCS, depicted in FIG. 1.

The orf E3L homolog (provided by Andrew Mercer, University of Otago, New Zealand as a restriction fragment of orf virus genome cloned into pVU plasmid) was amplified by polymerase chain reaction (melting temperature 92° C. for 1 minute, annealing temperature 50° C. for 2 minutes and extension temperature 72° C. for 3 minutes for 25 cycles) using gene specific primers containing BamHI and HindIII restriction sites (5'CTATGGATCCACAATGGCCTGCGAGTGC3' and 5'ATCTAAGCTTAATTAGAAGCTGATGCCGC3'). This amplified gene was digested by treatment with BamHI and HindIII and subcloned into pMPE3ΔGPTMCS by ligation into the same sites.

In vivo recombination was performed in baby hamster kidney BHK-21 cells. Lipofect-ACE (GIBCO, Gaithersburg, Md.) was used for transfection as per the manufacturer's directions, in conjunction with infections. Fifty percent confluent BHK-21 cells were infected at a multiplicity of infection (MOI) of 5 with E3L-deleted VV (WRΔE3L, which is the WR strain of vaccinia virus containing a lacZ gene in the locus at which E3L was deleted) resulting in the formation of blue plaques by this virus. DNA was mixed with LipofectACE (GIBCO) according to the manufacturer's instruction, and the mixture was added to the cells. Antibiotic-free complete medium was added to cells which were then placed in a $CO_2$ incubator at 37° C. for 36 hours to allow recombination between the plasmid and virus to take place; the cells were then harvested into the growth medium, centrifuged for 10 min at 1000×g at 4° C., and resuspended in 200 ul of complete medium containing 2% FBS.

Virus was extracted from transfected/infected cells by three rounds of freezing and thawing and used to infect confluent BHK-21 cells that had been pretreated for 6 hours with ecogpt selection medium: 40 ml of complete medium containing 5% FBS, 0.4 mg of mycophenolic acid (MPA), 10 mg of xanthine, and 0.6 mg of hypoxanthine. After a 1 hour infection, ecogpt selection medium was added to each plate and cells were allowed to grow at 37° C. until plaques were clearly visible (2 to 4 days).

On the appearance of plaques, the cells were overlaid with ecogpt selection medium containing 0.5% agarose and 0.04% X-gal (5-bromo-4 chloro-3 indolyl-β-galactoside). Six hours after overlaying, blue plaques were picked into 200 ul 1 mM Tris HCl pH 8.8 and subjected to three rounds of freeze-thawing. Two more rounds of plaque purification were performed by repeating the above steps. Each plaque was then amplified in BHK-21 cells in the absence of the ecogpt selection media for 48 hours. The virus infected cells were harvested and subjected to freeze thaws. Following the freeze-thaw procedure, serial dilutions of this amplified stock were used to infect confluent rabbit kidney RK-13 cells, which were then incubated in complete medium containing 5% FBS (no selection medium). During this incubation, a second recombination event takes place, which results in either recovery of the original virus (WRΔE3L) or of recombinant virus containing the inserted orf E3L homolog. Two days after this infection, the medium was replaced with an overlay containing 0.5% agarose, 0.04% X-Gal (5-bromo-4-chloro-3-indolyl-β-galactoside), and 5% FBS in complete medium.

Ten colorless plaques were picked from the overlaid plate and suspended in 200 ul of 1 mM Tris HCl pH 8.8. Colorless plaques indicate the presence of virus containing the orf E3L gene (the lacZ gene has been replaced by the orf E3L gene). Each of these plaques were amplified in BHK-21 to prepare virus stocks. Each of the virus stocks was sequenced to confirm that the gene in the E3L locus was orf E3L homolog.

EXAMPLE 2

Infection with WR, WRΔ3L and WRorfE3L

Wild-type vaccinia virus of the WR strain (wt WR) and variants WRΔE3L and WRorfE3L as described in Example 1 were assessed for pathogenicity as follows.

Groups of five c57b16 mice at four weeks of age were infected with different doses ($10^4$ plaque forming units (pfu), $10^5$ pfu and $10^6$ pfu) of WR, WRΔE3L and WRorfE3L by intranasal administration, and observed daily for death. Groups of six c57b16 mice at four weeks of age were infected with the same doses of these viruses by intracranial injection and observed daily for death.

Figure 2:
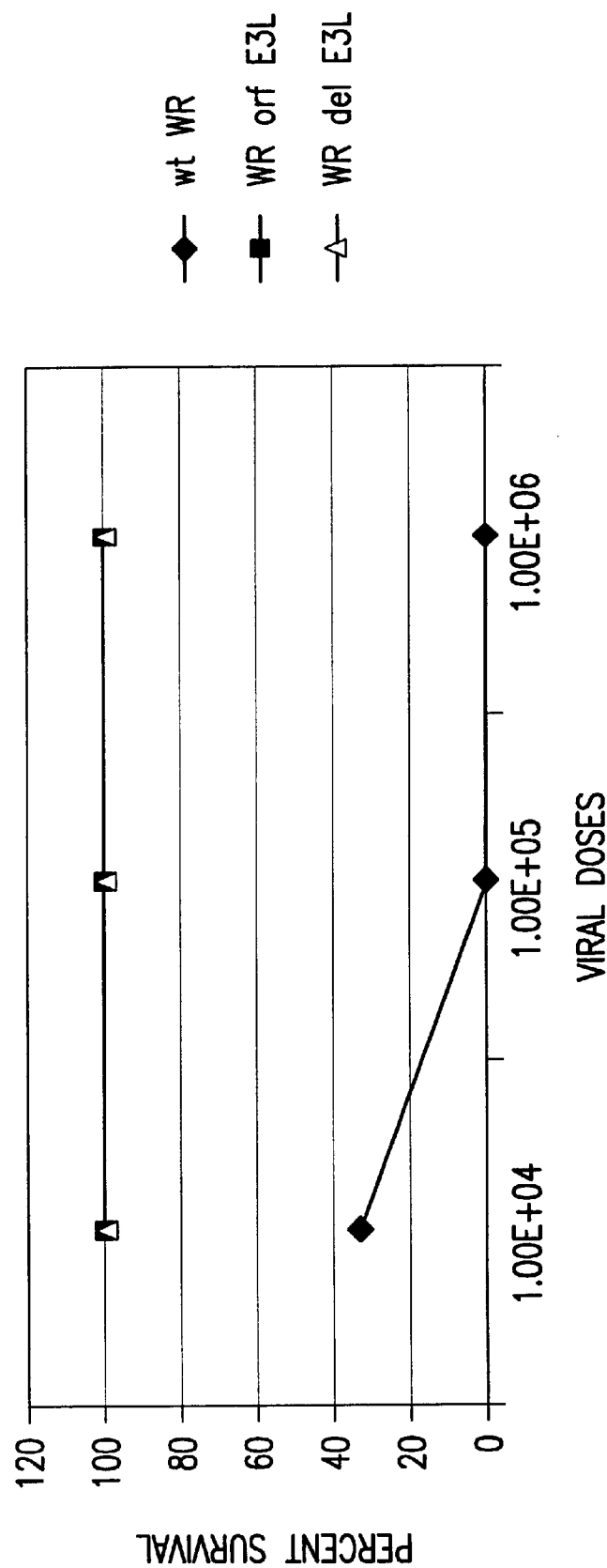
FIG. 2 is a graph depicting survival of mice following intranasal injection with vaccinia virus.

As shown in FIG. 2, intranasal infection with WR had an $LD_{50}$ less than $10^4$ pfu, whereas no pathogenesis could be detected with WRΔE3L or WRorfE3L even at the highest dose ($10^6$ pfu). These results indicate that the recombinant virus expressing the orf E3L homolog is over 1000 fold less pathogenic than wild type vaccinia virus of the WR strain.

EXAMPLE 3

Tissue Distribution of Virus

Figure 3:
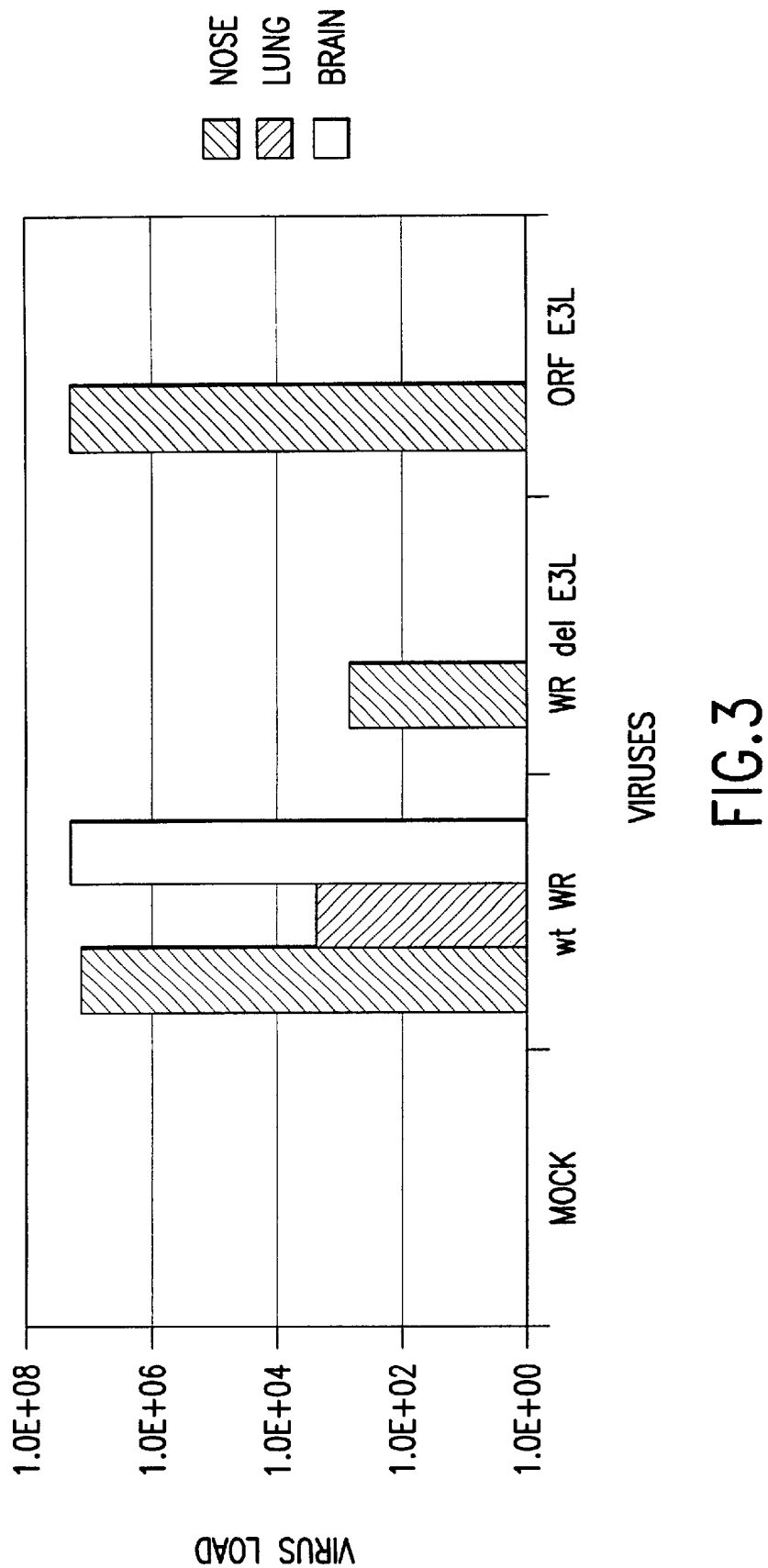
FIG. 3 is a graph depicting tissue distribution of vaccinia virus after intranasal injection.

Groups of three c57b16 mice were injected with $10^6$ pfu of wt WR, WRΔE3L and WRorfE3L by intranasal administration. Nasal turbinates, lung and brain were harvested, processed and titrated in an RK-13 cell line five days post infection. As shown in FIG. 3, wt WR was detected in nasal turbinates, lung and brain. The WRorfE3L was detected in nasal turbinates, but unlike wt WR, it did not spread to lung and brain following intranasal injection.

EXAMPLE 4

Vaccination with WRorfE3L

Figure 4:
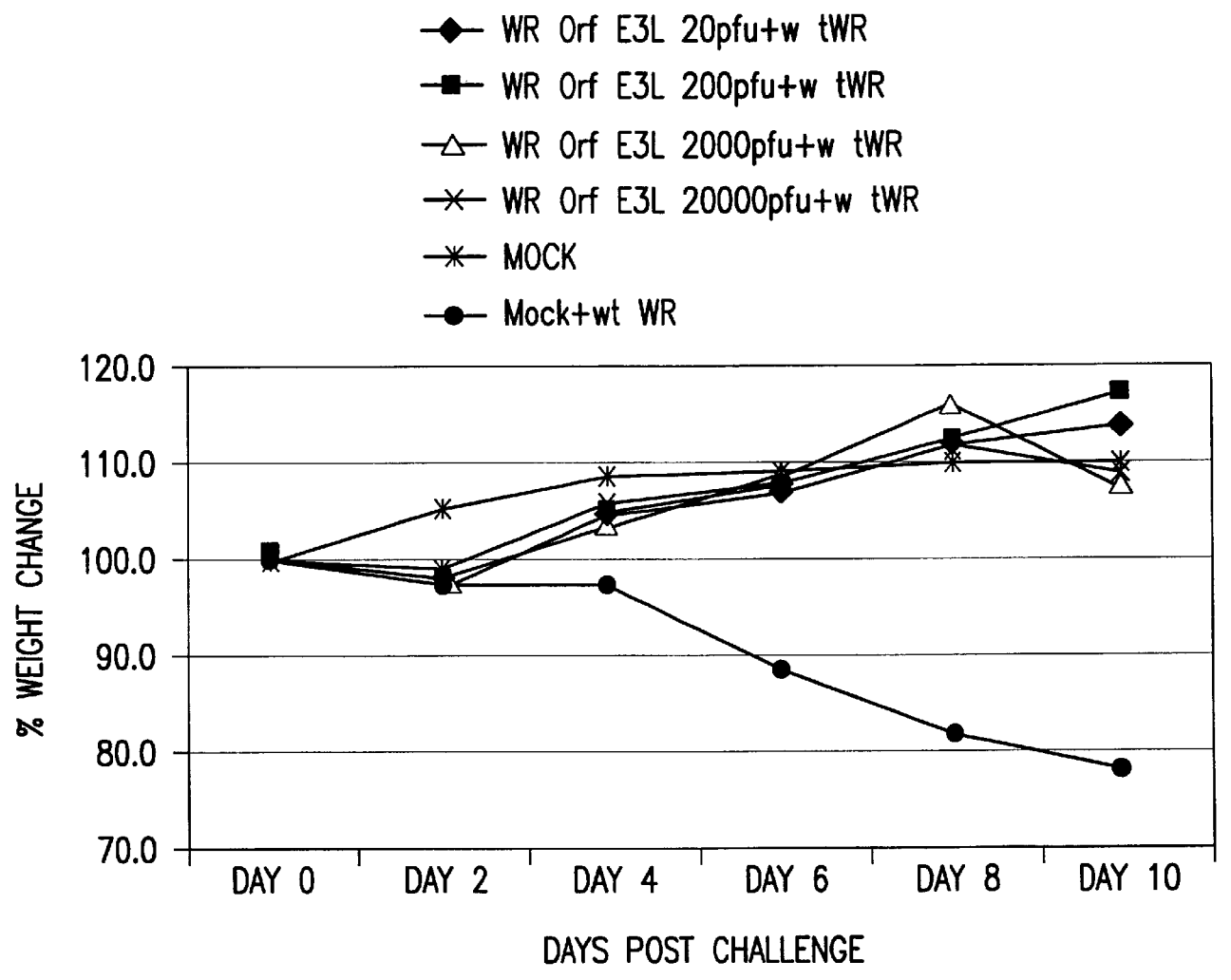

Groups of five c57b16 mice were immunized with different doses (ranging from 20 to 20,000 pfu) of WRorfE3L. One month later the immunized mice and the unimmunized controls (mock) were challenged with a million pfu of wt WR. Weight loss was used as an indicator of disease due to wt WR. As shown in FIG. 4, severe weight loss was observed in the unimmunized control while all the immunized mice recorded normal weight gain following challenge. Even 20 pfu of the recombinant virus was sufficient to protect mice against infection with wt WR.

We claim:

1. Vaccinia virus in which the E3L gene is replaced by a gene encoding an E3L homolog from the orf virus.

2. An expression vector comprising a vaccinia virus in which the E3L gene is replaced by a gene encoding an E3L homolog from the orf virus wherein said vector further comprises exogenous DNA operably linked to regulatory elements that control expression of said exogenous DNA.

3. The expression vector of claim 2 in which one or more non-essential virus-encoded gene functions have been deleted from the vaccinia virus.

4. A composition comprising the expression vector of claim 2 and a carrier.

5. A method of making a recombinant gene product comprising subjecting an expression vector comprising a vaccinia virus in which the E3L gene is replaced by a gene encoding an E3L homolog from the orf virus wherein said vector further comprises exogenous DNA operably linked to regulatory elements that control expression of said exogenous DNA to conditions whereby said recombinant gene product is expressed.

6. The method of claim 5 further comprising recovering said recombinant gene product.

7. Recombinant vaccinia virus WR orf E3L.

* * * * *

UNITED STATES PATENT AND TRADEMARK OFFICE
CERTIFICATE OF CORRECTION

PATENT NO. : 6,372,455 B1
DATED : April 16, 2002
INVENTOR(S) : Jacobs et al.

It is certified that error appears in the above-identified patent and that said Letters Patent is hereby corrected as shown below:

Column 1,
Line 67, "neurovirolence" should read -- neurovirulence --

Column 2,
Line 12, "firther" should read -- further --
Line 22, "linled" should read -- linked --

Column 4,
Line 32, "ul" should read -- µl --
Line 47, "ul" should read -- µl --
Line 66, "ul" should read -- µl --

Signed and Sealed this

First Day of October, 2002

Attest:

Attesting Officer

JAMES E. ROGAN
Director of the United States Patent and Trademark Office